United States Patent [19]

Stepniewski

[11] Patent Number: 5,648,066

[45] Date of Patent: Jul. 15, 1997

[54] SOLID SILICONE COMPOSITIONS AND METHODS FOR THEIR PREPARATION AND USE

[75] Inventor: George J. Stepniewski, Melville, N.Y.

[73] Assignee: Estee Lauder Companies, Melville, N.Y.

[21] Appl. No.: 538,550

[22] Filed: Oct. 3, 1995

[51] Int. Cl.$^6$ ...................................................... A61K 7/00
[52] U.S. Cl. ........................... 424/64; 424/401; 424/59; 424/70.12; 525/106
[58] Field of Search .............................. 424/64, 401, 59, 424/70.12; 525/106

[56] References Cited

U.S. PATENT DOCUMENTS

| | | | |
|---|---|---|---|
| 4,990,561 | 2/1991 | Yoshioka | 524/763 |
| 5,080,889 | 1/1992 | Katada et al. | 424/63 |
| 5,102,656 | 4/1992 | Kasat | 424/66 |
| 5,122,519 | 6/1992 | Ritter | 514/152 |
| 5,213,716 | 5/1993 | Patel et al. | 252/547 |

FOREIGN PATENT DOCUMENTS 61-069711  4/1986  Japan.

*Primary Examiner*—Margaret W. Glass
*Attorney, Agent, or Firm*—Karen A. Lowney, Esq.; Isaac D. Cohen

[57] ABSTRACT

Disclosed are solid silicone compositions comprising low molecular weight polyethylene solidifying agents and one or more non-volatile silicone fluids, along with a method for their preparation. The compositions are suitable for topical application to skin or hair, and are particularly useful in the preparation of novel skin treatment, hair treatment, lipstick and makeup products.

25 Claims, No Drawings

SOLID SILICONE COMPOSITIONS AND METHODS FOR THEIR PREPARATION AND USE

FIELD OF THE INVENTION

The present invention relates to solid silicone compositions suitable for topical application to human skin or hair. In particular, the invention relates to solid silicone compositions comprising a low molecular weight polyethylene solidifying agent and one or more non-volatile silicone fluids. The invention additionally relates to methods for the preparation and use of such compositions.

BACKGROUND OF THE INVENTION

Silicones are rapidly becoming ubiquitous components of pharmaceutical and personal care products. Their remarkably high thermal and chemical stability, their unusual ability to resist adhering to other materials and their aesthetically unique and pleasing tactile characteristics have made silicones invaluable raw materials in products designed for topical application to the skin or hair, such as skin treatment preparations, hair conditioners, lipsticks and makeup products. Such products are often desirably formulated in the form of sticks or gels for the elegance and ease of application these product forms offer to the consumer.

The term "silicones" actually encompasses a large and diverse group of polymeric fluids, oils, rubbers, resins and gums generally based on the structural unit —$R_2SiO$—, with R being a monovalent organic radical. The type and size of the radical(s) present (e.g., alkyl vs. aryl), the type and degree of polymerization (e.g., linear vs. cyclic), and the presence or absence of crosslinking, all affect the physical and chemical properties of the resultant silicone polymers.

Silicone fluids may be broadly classified as being either volatile or non-volatile, depending on how large a vapor pressure they possess at ambient temperature and pressure. Silicone fluids may also be characterized by their degree of viscosity, where viscosity is defined as resistance to flow and is commonly measured in centistokes. For a particular silicone polymer the viscosity generally increases, and the volatility generally decreases, as the molecular weight of the polymer increases.

Commercially available volatile silicone fluids include hexamethyldisiloxane [$(CH_3)_3SiOSi(CH_3)_3$]; methylated cyclic silicones (also referred to as cyclomethicones) which include octamethylcyclotetrasiloxane, an eight-membered ring compound formed from four Si—$(CH_3)_3$—O groups, and decamethylcyclopentasiloxane, a ten-membered ring compound formed from five Si—$(CH_3)_2$—O groups; and dimethicones having a viscosity of 10 centistokes or less. Dimethicones are linear silicone polymers conforming to the structure:

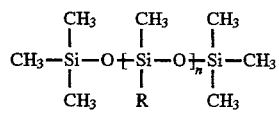

wherein R is methyl.

Volatile silicone fluids are generally compatible with many of the lipophilic materials commonly employed in topical compositions. They are use in such compositions for their ability to act as co-solvents, as well as to provide a dry, non-greasy feel to the compositions during application to the skin or hair.

Commercially available non-volatile silicone fluids include dimethicones having a viscosity of greater than 10 centistokes, alkylated dimethicones such as cetyl dimethicone (I, R=a mixture of $CH_3$ and $C_{16}H_{33}$), and trimethicones such as phenyl trimethicone (II):

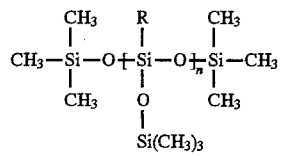

wherein R is phenyl.

Non-volatile silicone fluids are used in topical compositions to provide a slippery yet non-greasy feel to the compositions, and to provide an occlusive, water-resistant and emollient film to the skin surface upon topical application. They are also used as conditioners in hair treatment products, and as emulsion stabilizers in products formulated as oil-in-water or water-in-oil emulsions. Non-volatile silicone fluids are markedly less compatible than their volatile counterparts with many of the lipophilic materials commonly used in topical compositions.

Silicone gums are non-volatile silicone fluids possessing particularly high viscosities and molecular weights, and include dimethicones having viscosities of about 1,000,000 centistokes. Such gums are used in topical compositions for their unique tactile and film-forming properties, and are available commercially both in gum form and as free-flowing dispersions in silicone fluid carriers.

It is known in the art that polyethylenes are useful gelling agents for volatile silicone fluids. Polyethylenes are polymers of ethylene monomers that conform generally to the formula $(C_2H_4)_n$, wherein n is usually large enough such that the resultant polymers have average molecular weights of from about 1500 to about 100,000.

U.S. Pat. No. 5,122,519 to Ritter discloses topical gel formulations containing a tetracycline antibiotic, a volatile silicone solvent, an emollient ester co-solvent and a polyethylene gelling agent.

U.S. Pat. No. 5,102,656 to Kasat discloses, inter alia, antiperspirant creams containing a volatile silicone, a polyethylene gelling agent, and an antiperspirant active.

Japanese Published Unexamined Application JP 61069711A discloses, inter alia, solid cosmetic compositions containing a volatile silicone oil, a polyethylene gelling agent and a powder substrate.

The use of polyethylenes as solidifying agents for non-volatile silicone fluids has not been heretofore disclosed. In fact, most commercially available polyethylenes are known to be only minimally soluble in, and hence incompatible with, many of the non-volatile silicones used in topical compositions.

It has now been discovered that low molecular weight polyethylenes, i.e., polyethylenes having an average molecular weight of less than about 1,000, are excellent solidifying agents for silicone fluids. In particular, it has been surprisingly and unexpectedly discovered that such low molecular weight polyethylenes are excellent solidifying agents for non-volatile silicone fluids. It has also been surprisingly and unexpectedly discovered that compositions prepared from low molecular weight polyethylenes and non-volatile silicone fluids are stable, aesthetically elegant and useful in the preparation of novel skin treatment, hair treatment, lipstick and makeup products.

It is therefore an object of the present invention to provide solid silicone compositions suitable for topical application to human skin or hair which contain non-volatile silicone fluids. It is also an object of this invention to provide solid silicone compositions comprising a low molecular weight polyethylene solidifying agent and one or more non-volatile silicone fluids. Further objects of this invention are to provide a method for the preparation of such solid silicone compositions, and to provide skin treatment, hair treatment, lipstick and makeup compositions comprising the solid silicone compositions of the invention.

SUMMARY OF THE INVENTION

In accordance with the present invention there are provided solid silicone compositions suitable for topical application to human skin or hair which comprise:

(a) from about 3 to about 20 weight percent of a polyethylene solidifying agent having an average molecular weight of less than about 1,000; and (b) from about 20 to about 97 weight percent of a non-volatile silicone fluid.

The present invention additionally relates to a method for preparing such compositions, the method comprising the steps of:

(a) mixing a non-volatile silicone fluid with a polyethylene solidifying agent having an average molecular weight of less than about 1,000 at a temperature and for a time sufficient to dissolve the polyethylene solidifying agent in the silicone fluid, the amount of materials being adjusted such that the resultant mixture contains from about 3 to about 20 weight percent of the polyethylene solidifying agent and from about 20 to about 97 weight percent of the silicone fluid; and (b) allowing the mixture to cool to about ambient temperature.

It is to be understood that the terms "mixture" and "mixing" in this application are used in the broad sense of the words with the term "mixing" including, but not being limited to, stirring, blending, dispersing, milling, homogenizing and the like.

The solid silicone compositions of the present invention are stable against both physical and chemical degradation during extended storage, over a wide temperature range. They are aesthetically elegant and non-irritating upon application to the skin or hair, and provide an occlusive, water-resistant and emollient film upon topical application. The compositions of the invention are particularly useful in the preparation of skin treatment, hair conditioner, lipstick and makeup products.

DETAILED DESCRIPTION OF THE INVENTION

As mentioned hereinabove, the present invention provides solid silicone compositions suitable for topical application to human skin or hair which comprise:

(a) from about 3 to about 20 weight percent of a polyethylene solidifying agent having an average molecular weight of less than about 1,000; and (b) from about 20 to about 97 weight percent of a non-volatile silicone fluid.

The compositions comprise from about 3 to about 20 weight percent, preferably from about 3 to about 12 percent and more preferably about 10 weight percent of the low molecular weight polyethylene solidifying agent. The polyethylene solidifying agent preferably has an average molecular weight of from about 200 to about 800, more preferably from about 400 to about 600, most preferably about 500. In an especially preferred embodiment of the invention the polyethylene solidifying agent is a straight-chain homopolymer of polyethylene having an average molecular weight of about 500, as measured by vapor phase osmometry, available commercially from Petrolite Corporation, Polymers Division (Tulsa, Olka.) under the tradename Siltek PL.

In addition to the polyethylene solidifying agent, the compositions comprise from about 20 to about 97 weight percent of a non-volatile silicone fluid. In a first preferred embodiment of the invention the non-volatile silicone fluid comprises a dimethicone having a viscosity of from about 10 to about 50 centistokes, especially a dimethicone having a viscosity of about 20 centistokes. In a second preferred embodiment of the invention the non-volatile silicone fluid comprises a phenyl trimethicone having a viscosity of from about 10 to about 1150 centistokes, especially a phenyl trimethicone having a viscosity of from about 12 to about 56 centistokes. In a third preferred embodiment of the invention the non-volatile silicone fluid comprises a mixture of a dimethicone and a phenyl trimethicone, especially a mixture of a dimethicone having a viscosity of from about 10 to about 1000 centistokes and a phenyl trimethicone having a viscosity of from about 12 to about 56 centistokes.

In a preferred embodiment of the present invention the silicone fluid comprises one or more silicone gums. One such silicone gum is available commercially under the tradename SE-30 Silicone Gum from GE Silicones (Waterford, N.Y.). The silicone gum may be introduced into the compositions either in gum form or as a dispersion in other silicone fluids. Such dispersions are available commercially from GE Silicones, Dow Corning Corporation (Mt. Olive, N.J.), and Grant Industries, Inc. (Elmwood Park, N.J.).

The compositions of this invention additionally may comprise one or more pharmaceutically or cosmetically acceptable materials which are soluble in, or otherwise compatible with, the silicone fluid(s). "Pharmaceutically or cosmetically acceptable" as used herein refers to materials that are not known to be harmful to humans. These materials can be found for example in the CTFA International Dictionary of Cosmetic Ingredients as well as the U.S. Pharmacopeia or equivalent sources. Suitable cosmetically or pharmaceutically acceptable material for purposes of the present invention include, but are not limited to: oils; colorants; fragrances; sunscreens; stabilizers; preservatives; antioxidants; pharmacologically active materials; and mixtures thereof. The specific type and amount of pharmaceutically or cosmetically acceptable material used will vary with the desired physical, aesthetic and pharmacological properties of the final composition, and is readily determined by the skilled artisan.

In a preferred embodiment of the invention the compositions comprise one or more oils. The oils can function in the compositions as skin and hair conditioning agents, for example as emollients and occlusive agents. Emollients help maintain the softness, smoothness and pliability of skin and hair; occlusive agents minimize the evaporative loss of water from skin and hair surfaces.

Suitable oils include, but are not limited to: natural oils, especially squalane and jojoba oil; hydrocarbons; fatty alcohols; fatty acids; esters; sterols; and mixtures thereof. In a preferred embodiment the oil is an ester which is derived from a straight or branched chain fatty alcohol and/or a straight or branched chain fatty acid. Examples of emollient esters include: isopropyl myristate; isopropyl palmitate; isononyl isononanoate; isooctyl isononanoate; isononyl isomyristate; isodecyl isononanoate; and mixtures thereof. Preferably the oil is present in an amount of from about 0.5 to about 75.0 percent by weight of the total composition.

In another preferred embodiment of the invention the compositions comprise one or more colorants. Suitable colorants include, but are not limited to: dyes; stains; metal oxides, especially iron oxide and titanium dioxide; metal powders; and organic pigments. Preferably the colorant is present in an amount of from about 0.1 to about 30.0 percent by weight of the total composition.

In yet another preferred embodiment of the invention the compositions comprise one or more sunscreens. The term "sunscreen" as used herein refers to any material which is capable of protecting human skin from ultraviolet radiation having a wavelength of from about 280 to about 400 nm, by effectively absorbing such radiation, and/or reflecting or scattering such radiation away from the surface of the skin.

Suitable sunscreens include, but are not limited to: inorganic sunscreens, such as titanium dioxide and zinc oxide; organic sunscreens, such as 2-ethylhexyl p-methoxycinnamate; and mixtures thereof.

In yet another preferred embodiment of the invention the compositions include one or more pharmacologically active materials. Especially preferred as pharmacologically active materials are dermatologically active materials including, but not limited to: vitamins, such as vitamin E and vitamin E acetate; antiperspirant agents; antiacne agents; antidandruff agents; antifungal agents; antiinflammatory agents; and mixtures thereof.

As mentioned hereinabove, the present invention additionally relates to a method for preparing solid silicone compositions suitable for topical application to human skin or hair, the method comprising the steps of:

(a) mixing a non-volatile silicone fluid with a polyethylene solidifying agent having an average molecular weight of less than about 1,000 at a temperature and for a time sufficient to dissolve the polyethylene solidifying agent in the silicone fluid, the amount of materials being adjusted such that the resultant mixture contains from about 3 to about 20 weight percent of the polyethylene solidifying agent and from about 20 to about 97 weight percent of the silicone fluid;

(b) allowing the mixture to cool to about ambient temperature.

The optimal temperature and time sufficient to dissolve the polyethylene solidifying agent in the silicone fluid will vary with the exact materials used, and is readily determined by one skilled in the art. Generally speaking, a temperature of from about 90° to about 110° C., and usually from about 90° to 95° C., for a period of about 15 minutes is sufficient to accomplish this dissolution.

The compositions of the present invention may be formulated for a wide range of topical skin and hair applications. For example, the compositions may be formulated as lip area treatment preparations, eye area treatment preparations, sunscreen preparations, fragrance preparations, lipsticks, blushes, foundations, eyeshadows, hair conditioners and the like.

The following non-limiting examples illustrate various embodiments of the present invention:

EXAMPLES 1–3
SOLID SILICONE COMPOSITIONS

| INGREDIENT | WEIGHT PERCENT | | |
|---|---|---|---|
| | EXAMPLE 1 | EXAMPLE 2 | EXAMPLE 3 |
| Low Molecular Weight Polyethylene[1] | 10 | 10 | 10 |
| Dimethicone, 10 Centistokes[2] | 90 | — | — |
| Phenyl Trimethicone, 15–30 Centistokes[3] | — | 90 | — |
| Phenyl Trimethicone, 850–1150 Centistokes[4] | — | — | 90 |

[1]Siltek PL (Petrolite Corp., Polymers Division, Tulsa OK)
[2]Dow Corning 200 Fluid, 20 Centistokes (Dow Corning Corp., Mt. Olive, NJ)
[3]Silicone 556 Fluid (Dow Corning Corp., Mt. Olive, NJ)
[4]Abil AV 1000 (Goldschmidt Chemical Corp., Hopewell, VA)

PROCEDURE

For each of Examples 1–3, the low molecular weight polyethylene and the non-volatile silicone fluid were combined and heated with mixing to 90°–95° C. for about 15 minutes to effect complete dissolution of the polyethylene. The mixture was then allowed to cool to room temperature to afford a stable, cosmetically elegant solid composition suitable for topical application to human skin or hair.

EXAMPLE 4
LIPSTICK COMPOSITION

| INGREDIENT | WEIGHT PERCENT |
|---|---|
| Dimethicone, 200 Centistokes[1] | 21 |
| Phenyl Trimethicone, 35–56 Centistokes[2] | 50 |
| Dimethicone Gum[3] | 5 |
| Tocopheryl Acetate[4] | 2 |
| Jojoba Oil[5] | 2 |
| D&C Red No. 6 Barium Lake[6] | 5 |
| D&C Red No. 7 Calcium Lake[7] | 5 |
| Low Molecular Weight Polyethylene[8] | 10 |

[1]Dow Corning 200 Fluid, 20 Centistokes (Dow Corning Corp., Mt. Olive, NJ)
[2]Dow Corning 2-2757 Fluid (Dow Corning Corp., Mt. Olive, NJ)
[3]SE-30 Silicone Gum (GE Silicones (Waterford, NY)
[4]DL-α-Tocopheryl Acetate USP (Hoffmann - La Roche Inc., Nutley, NJ)
[5]Jojoba Oil Refined Grade (International Flora Technologies, Ltd., Gilbert, AZ)
[6,7]Sun Chemical Corp. (Staten Island, NY)
[8]Siltek PL (Petrolite Corp., Polymers Division, Tulsa OK)

PROCEDURE

The above ingredients were combined and heated with mixing to 90°–95° C. for about 15 minutes to effect complete dissolution of the polyethylene. The mixture was then allowed to cool to room temperature to afford a stable, cosmetically elegant lipstick composition.

While the present invention has been set forth in terms of specific embodiments thereof, it will be understood that numerous variations are now enabled to those skilled in the art. Accordingly, the invention is to be broadly construed and limited only by the scope of the appended claims.

What is claimed is:

1. A solid silicone composition suitable for topical application to human skin or hair which comprises:

(a) from about 3 to about 20 percent by weight of the total composition of a polyethylene solidifying agent which is a straight-chain homopolymer of polyethylene having an average molecular weight of about 500 or less as measured by vapor pressure osmometry; and (b) from about 20 to about 97 percent by weight of the total composition of a non-volatile silicone fluid.

2. The composition of claim 1 comprising from about 3 to about 12 percent by weight of the total composition of the polyethylene solidifying agent.

3. The composition of claim 2 comprising about 10 percent by weight of the total composition of the polyethylene solidifying agent.

4. The composition of claim 2 wherein the non-volatile silicone fluid is a dimethicone having a viscosity of from about 10 to about 50 centistokes.

5. The composition of claim 4 wherein the dimethicone has a viscosity of about 20 centistokes.

6. The composition of claim 1 wherein the non-volatile silicone fluid is a phenyl trimethicone having a viscosity of from about 10 to about 1150 centistokes.

7. The composition of claim 6 wherein the phenyl trimethicone has a viscosity of from about 12 to about 56 centistokes.

8. The composition of claim 1 wherein the non-volatile silicone fluid comprises a mixture of dimethicone and phenyl trimethicone.

9. The composition of claim 8 wherein the dimethicone has a viscosity of from about 10 to about 1,000 centistokes and the phenyl trimethicone has a viscosity of from about 12 to about 56 centistokes.

10. The composition of claim 1 wherein the silicone fluid comprises a silicone gum.

11. The composition of claim 1 additionally comprising a non-silicone fluid oil.

12. The composition of claim 11 wherein the oil is selected from the group consisting of jojoba oil and squalane.

13. The composition of claim 11 wherein the oil is selected from the group consisting of esters derived from fatty alcohols and esters derived from fatty acids.

14. The composition of claim 1 additionally comprising a colorant.

15. The composition of claim 14 wherein the colorant is selected from the group consisting of metal oxides and organic pigments.

16. The composition of claim 15 wherein the metal oxide is selected from the group consisting of titanium dioxide and iron oxide.

17. The composition of claim 1 additionally comprising a sunscreen.

18. The composition of claim 1 additionally comprising a pharmacologically active material.

19. The composition of claim 18 wherein the pharmacologically active material is a dermatologically active material.

20. A solid silicone composition suitable for topical application to human skin or hair which comprises:

(a) from about 3 to about 20 percent by weight of the total composition of a polyethylene solidifying agent which is a straight-chain homopolymer of polyethylene having an average molecular weight of about 500 or less as measured by vapor pressure osmometry;

(b) from about 20 to about 97 percent by weight of the total composition of a non-volatile silicone fluid comprising from about 0.5 to about 25 percent by weight of the total composition of a silicone gum;

(c) from about 0.5 to about 75 percent by weight of the total composition of a non-silicone fluid oil; and (d) from about 0.1 to about 30 percent by weight of the total composition of a colorant.

21. A method for preparing a solid silicone composition suitable for topical application to skin or hair, the method comprising the steps of:

(a) mixing a non-volatile silicone fluid with a polyethylene solidifying agent which is a straight-chain homopolymer of polyethylene having an average molecular weight of about 500 or less as measured by vapor pressure osmometry at a temperature and for a time sufficient to dissolve the polyethylene solidifying agent in the silicone fluid, the amount of materials being adjusted such that the resultant mixture contains from about 3 to about 20 percent by weight of the total composition of the polyethylene solidifying agent and from about 20 to about 97 percent by weight of the total composition of the silicone fluid;

(b) allowing the mixture to cool to about ambient temperature.

22. A solid silicone composition prepared according to the method of claim 21.

23. A skin treatment composition comprising the solid silicone composition of claims 1 or 22.

24. A lipstick composition comprising the solid silicone composition of claims 1 or 22.

25. A makeup composition comprising the solid silicone composition of claims 1 or 22.

* * * * *